United States Patent [19]

Credner et al.

[11] 4,123,534
[45] Oct. 31, 1978

[54] ADENINE DERIVATIVES AND HYPOLIPIDEMIC COMPOSITION THEREOF

[75] Inventors: Karl Credner, Kaarst; Günter Brenner, Grefrath; Manfred Tauscher, Gronau, Leine; Ljerka Jozic, Hannover, all of Fed. Rep. of Germany

[73] Assignee: Johann W. Wülfing, Fed. Rep. of Germany

[21] Appl. No.: 789,845

[22] Filed: Apr. 22, 1977

[30] Foreign Application Priority Data

Apr. 24, 1976 [GB] United Kingdom ............... 16720/76
Apr. 24, 1976 [GB] United Kingdom ............... 16721/76

[51] Int. Cl.$^2$ .................... C07D 473/34; A61K 31/52
[52] U.S. Cl. ...................................... 424/253; 544/277

[58] Field of Search .......................... 260/252; 424/253

[56] References Cited

U.S. PATENT DOCUMENTS 3,412,093 11/1968 Podesva et al. ...................... 260/252

FOREIGN PATENT DOCUMENTS 7,201,936 1/1972 Japan ...................................... 424/253

Primary Examiner—Paul M. Coughlan, Jr.
Assistant Examiner—D. B. Springer
Attorney, Agent, or Firm—Jacobs & Jacobs

[57] ABSTRACT

Adenine derivatives, their preparation and pharmaceutical compositions containing the same in an amount sufficient to effect hypolipidemia. The derivatives are not inhibitors of C-AMP-phosphodiesterase.

13 Claims, No Drawings

ADENINE DERIVATIVES AND HYPOLIPIDEMIC COMPOSITION THEREOF

The present invention relates to novel adenine derivatives, to a process for their preparation and to pharmaceutical compositions containing them.

Hyperlipidemia represents an increased health risk, since it promotes the development of arteriosclerosis. Lipid-concentration lowering preparations, which decrease the triglyceride, free fatty acids and cholesterol content in blood serum are therefore of great importance. Agents which have been used or suggested for the treatment of hyperlipidemia include clofribinic acid, nicotinic acid, 3-methylpyrazole-5-carboxylic acid and 3-methylisoxazolyl-5-carboxylic acid and their salts such as their salts with theophylline bases such as 2-hydroxy-3-(N-methyl-N-2-hydroxyethyl)-amino-propyltheophylline.

The present invention relates to 7- or 9-substituted adenine derivatives which can form salts with the above named acids and which, according to present knowledge, are not inhibitors of C - AMP - phosphodiesterase and which exhibit synergistic properties with the above acids.

The hypocholesterolemic agent lentinacin, which is a metabolite of the fungus hentinus edodes, is an adenine derivative which carries a 2,3-dihydroxybutyroyl group at the 9- position. This compound lowers all lipid components of the plasma - lipoproteins (cholesterol, triglycerides and phospholipids) in different animal species and in man [J. Med. Chem. 17, (1974), 846–855]. A large number of adenine derivatives were produced and it was shown that for lipid lowering action the intact adenine structure is necessary.

We have now discovered a distinct and novel group of adenine derivatives which are capable of enhancing the hypolipidemic effectiveness of certain hypolipedemically useful organic acids.

Accordingly the present invention provides the compounds of the formulae (I) and (II):

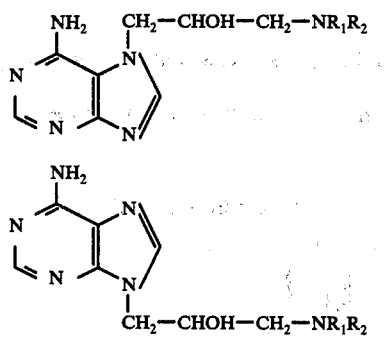

and acid-addition salts thereof wherein $R_1$ is an alkyl group of 1 to 4 carbon atoms, a hydroxyalkyl group of 2-4 carbon atoms, an alkoxyalkyl group of 2-6 carbon atoms; and $R_2$ is a hydrogen atom or an alkyl group of 1-4 carbon atoms, a hydroxyalkyl group of 2-4 carbon atoms or an alkoxyalkyl group of 2-6 carbon atoms.

Suitable values for $R_1$ include the hydrogen atom and methyl, ethyl, n-propyl, n-butyl, 2-hydroxyethyl, 2-methoxyethyl, 2-ethoxyethyl, 2-hydroxypropyl, 3-hydroxypropyl and the like. The iso-propyl group is also suitable as $R_1$.

Suitable values for $R_2$ include the hydrogen atom and those stated to be suitable for $R_1$.

Particulary suitable values for $R_1$ include the 2-hydroxyethyl group.

Thus particularly suitable compounds of the formulae (I) and (II) include those of the formulae (III) and (IV):

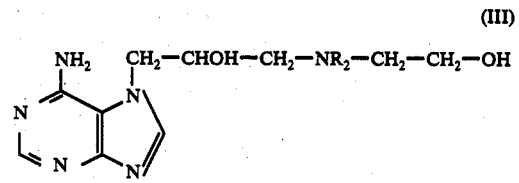

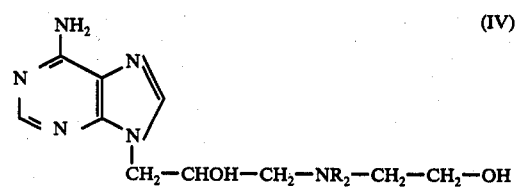

and acid addition salts thereof.

Highly favoured values for the group $R_2$ in the compounds of formulae (I)–(IV) include the hydrogen atom and $C_{1-4}$ alkyl groups such as the methyl group.

A preferred group $R_2$ for inclusion in the compounds of the formulae (I)–(IV) is the methyl group.

The compounds of the formulae (I)–(IV) are nitrogenous bases which can form acid addition salts with inorganic or organic acid in conventional manner. Suitable acids for such a purpose include hydrochloric, phosphoric, methane sulphonic, toluene sulphonic, acetic, citric, lactic, tartaric, acetylsalicylic, orotic, theophyllinylacetic, fusaric, 5-chloroindolecarboxylic, 2,5-dihydroxybenzoic, nicotinic, 3-methylpyrazole-5-carboxylic, 3-methylisoxazole-5-carboxylic, succinic and other pharmaceutically acceptable acids.

Salts of certain pharmaceutically acceptable acids with the compounds of the formulae (I)–(IV) can exhibit a significantly stronger pharmacological effect than the acid per se. This enhancement in activity is surprising in view of the general lack of effectiveness of the compounds of the formulae (I)–(IV) per se. Thus an important aspect of this invention comprises the acid addition salts of the compounds of the formulae (I)–(IV) with pharmacologically active acids selected from 3-methylpyrazole-5-carboxylic, 3-methylisoxazole-5-carboxylic, acetylsalicylic, clofibric, nicotinic, fusaric, theophyllinylacetic, orotic and 5-chloroindole carboxylic acids.

Particularly suitable salts of this invention include those between a compound of the formulae (I)–(IV) and nicotinic, acetylsalicylic, 3-methylpyrazole-5-carboxylic and 3-methylisoxazole-5-carboxylic acid.

Preferred salts of this invention include those between a compound of the formula (III) or (IV) and 3-methylpyrazole-5-carboxylic acid.

The present invention also provides a pharmaceutical composition which comprises a compound of the formulae (I)–(IV) or a salt thereof together with a pharmaceutically acceptable carrier.

Most suitably such compositions comprise a salt of a compound of the formulae (I)–(IV) with a pharmaceutically active acid as hereinbefore described.

The compositions of the invention are specially useful in treating adverse hyperlipidemic states in humans. For such treatment, the compounds are generally administered orally although parenteral methods of administration may also be used.

Typical oral formulations will include tablets, pills, capsules, sachets, granules, powders, chewing gum, suspensions, emulsions and solutions, particularly preferred oral formulations are tablets and capsules. Where appropriate, the formulations may include conventional diluents, binding agents, dispersing agents, surface-active agents, lubricating agents, coating materials, flavouring agents, colouring agents, solvents, thickening agents, suspending agents, sweeteners or any other pharmaceutically acceptable additives, for example, gelatin, lactose, starch, talc, magnesium stearate, hydrogenated oils, polyglycols and syrups. Where the formulations are tablets or capsules and the like, they will represent pre-measured unit doses but in the case of granules, powders, suspensions and the like, the formulations may be presented as pre-measured unit doses or in multi-dose containers from which the appropriate unit dose may be withdrawn.

Injectable compositions may be as aqueous or non-aqueous solutions, suspensions or emulsions in a pharmaceutically acceptable liquid (e.g. sterile pyrogen-free water or parenterally acceptable oils) or mixtures of liquids which may contain bacteriostatic agents, antioxidants or other preservatives, buffers, (preferably in the physiological pH range of 6.5–7.0), solutes to render the solution isotonic with the blood, thickening agents, suspending agents or other pharmaceutically acceptable additives. Such forms will be presented in unit dose forms such as ampoules or disposable injection devices or in multi-dose forms such as a bottle from which the appropriate dose may be withdrawn, or as a solid form or concentrate which can be used to quickly prepare an injectable formulation.

Preferred dosage forms of the composition will be conventional tablets or capsules containing a pre-measured dose for oral administration. Such dosage forms will normally contain between 0.25 and 100 mgs. of a compound of formula (III) and generally between 0.5 and 50 mgs., preferably from about 1 to 25 mgs. Such dosage forms will normally be taken from 1 to 6 times daily. The maximum daily dose for a 70 kg. adult will not normally exceed 100 mgs. and will not usually exceed 75 mgs. A daily dose of not more than 50 mgs. is generally preferred. Normally, the daily dose for a 70 kg. adult will be at least 10 mgs., usually at least 25 mgs.

The compositions of the invention may be prepared by conventional methods of mixing, blending, tabletting and the like.

The present invention also provides a process for the preparation of a compound of the formulae (I) and (II) as hereinbefore defined which process comprises:

a. The alkylation of a basic salt of the compound of the formula (V):

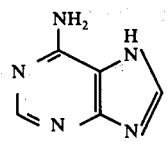  (V)

with a compound of the formula (VI):

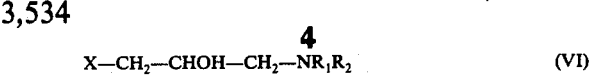  (VI)

wherein $R_1$ and $R_2$ are as defined in relation to formulae (I) and (II) and X is a readily displaceable group.

b. The reaction of formamide with a compound of the formula (VII) or (VIII):

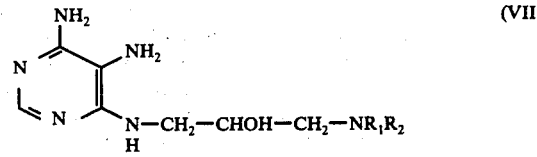  (VII)

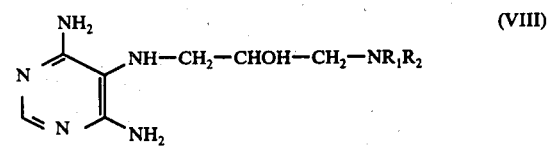  (VIII)

wherein $R_1$ and $R_2$ are as defined in relation to formula (I) or (II).

c. The reaction of a compound of the formula (IX) or (X):

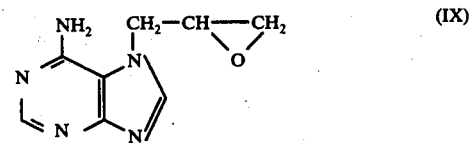  (IX)

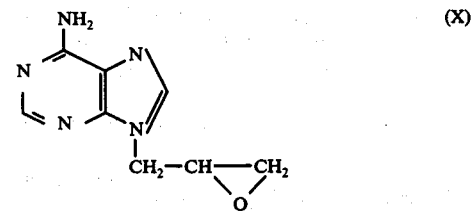  (X)

with an amine of the formula (XI):

  (XI)

wherein $R_1$ and $R_2$ are as defined in relation to formula (I) or (II).

d. The reaction of a compound of the formula (XII) or (XIII):

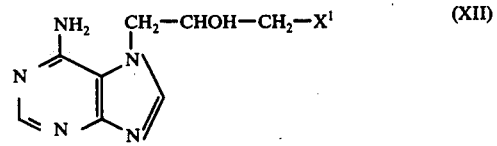  (XII)

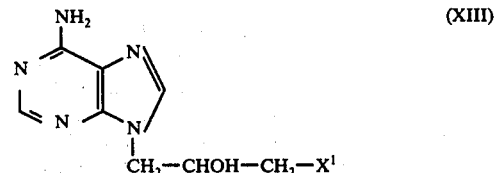  (XIII)

wherein $X^1$ is a displaceable group with an amine of the formula (XI) as hereinbefore defined.

e. The reduction of a compound of the formula (XIV) of (XV):

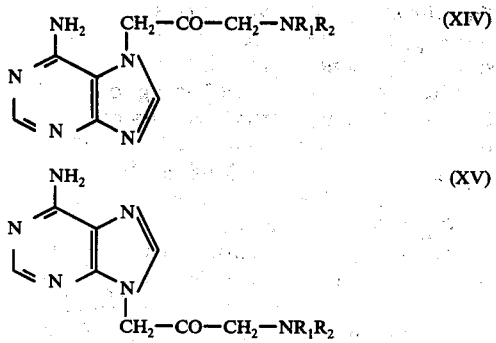

wherein R₁ and R₂ are as defined in relation to formulae (I) and (II).

f. The alkylation of a basic compound of the formula (V) or a salt thereof with a compound of the formula (XVI):

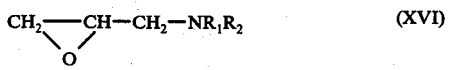

wherein R₁ and R₂ are as defined in relation to formulae (I) and (II).

g. The removal of an N- or O- protecting group from a corresponding N-protected or O-protected compound.

h. Any other method known per se.

Particularly suitable methods of preparing the compounds of the formulae (I)–(IV) are believed to be those outlined in the preceding schemes a. and b. and particularly that of a.

Such alkylation reactions are normally carried out in an inert organic solvent such as a lower alkanol, for example, ethanol, isopropanol or the like. The reaction may take place at any non-extreme temperature but conveniently short reaction times result if a somewhat elevated temperature is employed, for example 40°–120° C., more usually about 60°–100° C., for example about 80° C.

Normally the alkylation reaction is performed on a salt of 6-aminopurine such as the sodium, potassium or like salt. If desired these salts may be pre-formed or may be formed in situ by reaction with a base such as sodium carbonate, potassium carbonate or the like.

The group X present in the compound of the formula (VI) may be any conventional good leaving group such as a chlorine or bromine atom or a methanesulphonate or toluenesulphonate group or the like. A particularly convenient value for the group X is the chlorine atom.

The compounds of the formulae (VII) and (VIII) as hereinbefore described may be prepared by the reduction of corresponding nitro-compounds in which the 4-amino group is also optionally protected for example by benzoylation.

The salts of the compounds of the formulae (I)–(IV) may be prepared in any conventional manner, for example, by the reaction of the base of the formulae (I)–(IV) with an acid in a solvent.

If desired the compounds of the formulae (I)–(IV) may be prepared and used as a pure optical isomer or as a mixture of such isomers, for example a fully racemic mixture.

The invention is illustrated by the following Examples:

EXAMPLE 1

6-Amino-9-[2-hydroxy-3-(N-methyl-N-2-hydroxyethyl)aminopropyl]purine and
6-amino-7-[2-hydroxy-3-(N-methyl-N-2-hydroxyethyl)aminopropyl]purine.

To a stirred suspension of the potassium salt of adenine (17.4g) and potassium carbonate (10g) in isopropanol (120 ml) at 50°–60° C. was added dropwise 1-chloro-2-hydroxy-3-(N-methyl-N-2-hydroxyethyl)aminopropane (20.6g) in isopropanol (5 ml). The mixture was stirred for a further 1 hour at 80° C. under reflux and the mixture was then allowed to cool to room temperature. After filtration removal of the solvent under reduced pressure yielded a mixture of the title compounds (14.5g).

Careful recrystallisation from isopropanol and ethanol yielded the separated isomers (combined weight 9.9g).

The physical characteristics of the title compounds is given in Tables 1 and 2 hereinafter. The remaining compounds referred to in Tables 1 and 2 were prepared by strictly analogous procedures.

TABLE 1 a) 7-SUBSTITUTED ADENINS structure: adenine with N(7)—CH₂—CH(OH)—CH₂—N(R)—CH₂—CH₂—OH

| R | Molecular Weight | MP [° C] | UV [nm] | NMR [δ] for N(7)—CH₂— |
|---|---|---|---|---|
| —CH₂—CH₃ | 280,33 | 202–203 | 273 | 3,90–4,24 |
| —CH(CH₃)₂ | 294,35 | 221–222 | 273 | 3,84–4,10 |
| —(CH₂)₃—CH₃ | 308,38 | 195–197 | 273 | 3,83–4,19 |
| —CH₂—CH₂—OH | 296,33 | 176–178 | 273 | 3,90–4,10 |
| —CH₃ | 266,31 | 210–211 | 273 | 3,90–4,24 |

TABLE 2 b) 9-SUBSTITUTED ADENINS structure: adenine with N(9)—CH₂—CH(OH)—CH₂—N(R)—CH₂—CH₂—OH

| R | Molecular Weight | MP [° C] | UV [nm] | NMR [δ] for N(9)—CH₂— |
|---|---|---|---|---|
| —CH₂—CH₃ | 280,33 | 159–160 | 260 | 3,57–3,90 |
| —CH(CH₃)₂ | 294,35 | 141–143 | 260 | 3,57–4,10 |
| —(CH₂)₃—CH₃ | 308,38 | 121–122 | 260 | 3,57–4,46 |
| —CH₂—CH₂—OH | 296,33 | 139,141 | 260 | 3,57–4,20 |
| —CH₃ | 266,31 | 152–153 | 260 | 3,70–3,40 |

EXAMPLE 2

6-Amino-9-[2-hydroxy-3-(N-methyl-N-2-hydroxyethyl)aminopropyl]purine3-methylpyrazole-5-carboxylate To a refluxing solution of 6-amino-9-[2-hydroxyl-3-(N-methyl-N-2-hydroxyethyl) aminopropyl]purine (10.64g) in absolute ethanol (90 ml) was added a solution of 3-methylpyrazole-5-carboxylic acid (5.44g) in absolute ethanol (60 ml). On cooling a compound precipitated out and was filtered off, washed with a little cold ethanol and dried to yield the title compound as a crystalline product (12.3g), m.p. 154°–156° C.

EXAMPLE 3

6-Amino-9-[2-hydroxy-3-(N-2-hydroxyethyl-N-n-butyl)aminopropyl]purine 2,5-dihydroxybenzoate.

To a stirred refluxing solution of 6-amino-9-[2-hydroxy-3-(N-2-hydroxyethyl-N-n-butyl)amionpropyl]purine (3.1g) in methanol (60 ml) was added 2,5-dihydroxybenzoic acid. Stirring under reflux was continued until a clear solution was obtained. On cooling a compound precipitated out and was filtered off, washed with a little cool methanol and dried to yield the title compound as a crystalline material (3g), m.p. 163°–164° C.

When tested in normal rats starved for 17 hours and then dosed orally, it was found that the compound of Example 2 caused a reduction of about 30–40% in serum triglyceride levels 1 hour post administration over the dose range of 0.25 mg/kg to 25 mg/kg. Similarly, a reduction in serum free fatty acid concentration of about 40–50% was produced over the dose range 0.15 mg/kg to 5 mg/kg. Further, a reduction of about 30% in serum cholesterol levels was observed at a dose of 100 mg/kg.

The compound of the formula (IV) where R is a methyl group has a low acute toxicity, for example in mice the compound has an $LD_{50}$ of about 1g/kg by oral administration and about 350mg/kg by intra-venous administration.

When administered to male rats the 3-methylpyrazole-5-carboxylic acid addition salts of the compound of the formula (IV) wherein $R_2$ is respectively a methyl, ethyl, isopropyl and n-butyl at a dose of 1 mg/kg per os produced a fall in serum triglyceride levels of about 23%, 34%, 34% and 56% respectively.

EXAMPLE 5

Using the process of Examples 2 and 3, the following compounds were prepared.

(a) 9-Substitution:

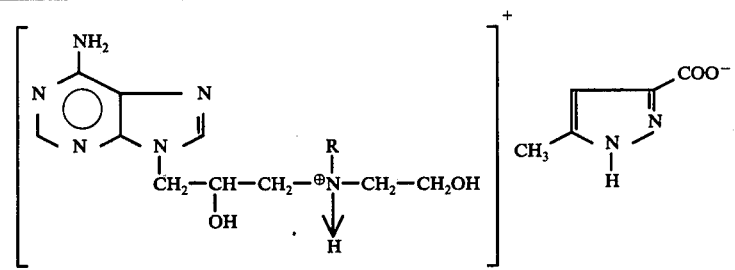

| EXAMPLE | R | MW | MP [° C] | C | H | O | N |
|---|---|---|---|---|---|---|---|
| | | | | calculated/found | | | |
| 1 | —CH₂—CH₃ | 406,5 | 115,5 –117,0 | 50,23 49,77 | 6,44 5,96 | 15,94 16,16 | 27,56 27,88 |
| 2 | —CH(CH₃)CH₃ | 420,5 | 147–149 | 51,41 51,05 | 6,71 6,86 | 15,21 15,06 | 26,64 27,06 |
| 3 | —(CH₂)₃—CH₃ | 434,5 | 142,5 –143,5 | 52,51 52,54 | 6,65 6,62 | 14,72 14,85 | 25,78 25,89 |
| 4 | —CH₂—CH₂—OH | 422,4 | 157–158 | 48,33 48,30 | 6,20 6,18 | 18,93 19,40 | 26,53 26,15 |

EXAMPLE 4

Demonstration of Pharmacological Effect (b) 7-Substitution:

| | | | | C | H | O | N |
|---|---|---|---|---|---|---|---|
| 5 | —CH₂ | 392,4 | 185–187 | 48,97 48,94 | 6,17 6,22 | 16,31 16,51 | 28,29 28,25 |

EXAMPLE 6

Using the process of Examples 2 and 3 the following salts of 6-amino-9-[2-hydroxy-3-(N-methyl-N-2-hydroxyethyl-amino)-propyl]-purine with pharmacologically active acids were prepared.

| ACID-ANION | MW | MP [° C] | CHN-ANALYSIS calculated / found | | | |
|---|---|---|---|---|---|---|
| | | | C | H | O | N |
| 5-methyl-isoxazol-3-carboxylate | 339,0 | 120 | 48,85 | 5,89 | 20,34 | 24,92 |
| | | | 48,95 | 6,08 | 20,12 | 24,99 |
| 3,4,5-trimethoxy-benzoate | 478,5 | 143 | 52,71 | 6,52 | 23,41 | 17,56 |
| | | | 52,82 | 6,75 | 22,40 | 17,90 |
| orotate | 422,0 | 225 | 45,50 | 5,25 | 22,73 | 26,53 |
| | | | 45,52 | 5,35 | 23,03 | 26,23 |
| theophyllin-7-acetate | 504,5 | 117–118 | 47,61 | 5,59 | 19,02 | 27,76 |
| | | | 47,35 | 6,12 | 18,52 | 28,10 |
| 5-chloroindol-2-carboxylate | 461,9 | 125 | 52,00 | 5,24 | 13,85 | 21,23 |
| | | | 52,12 | 5,24 | 14,55 | 21,31 |
| flufenaminate | 547,5 | 136 | 54,84 | 5,15 | | 17,91 |
| | | | 55,07 | 5,19 | | 17,78 |

EXAMPLE 7

Using the process of Examples 2 and 3,6-amino-9-[2-hydroxy-3-(N-di-(2-hydroxyethyl-amino)-propyl]purine-nicotinate has been prepared, m.pt. 102°–104° C.

What we claim is:

1. An acid addition salt of an amine of the formula:

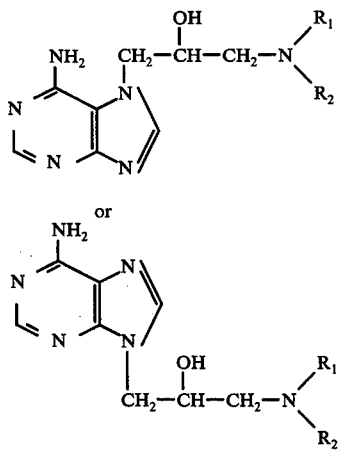

wherein
$R_1$ is alkyl of 1 to 4 carbon atoms, hydroxyalkyl of 2 to 4 carbon atoms or alkoxyalkyl of 2 to 6 carbon atoms; and
$R_2$ is hydrogen, alkyl of 1 to 4 carbon atoms; hydroxyalkyl of 2 to 4 carbon atoms or alkoxyalkyl of 2 to 6 carbon atoms;
and an acid selected from the group consisting of 3-methylpyrazole-5-carboxylic acid, 3-methylisoxazole-5-carboxylic acid, acetylsalicylic acid, clofibric acid, nicotinic acid, fusaric acid, theophyllinyl-7-acetic acid, orotic acid, 5-chloroindole-2-carboxylic acid, 5-methylisoxozole-3-carboxylic acid, 3,4,5,-trimethoxybenzoic acid and flufenamic acid.

2. A salt according to claim 1 wherein $R_1$ is 2-hydroxyethyl.

3. A salt according to claim 2 wherein $R_2$ is hydrogen or alkyl of 1 to 4 carbon atoms.

4. A salt according to claim 2 wherein $R_2$ is hydrogen, methyl, ethyl, isopropyl, n-butyl or 2-hydroxyethyl.

5. A salt according to claim 2 wherein said acid is 3-methylpyrazole-5-carboxylic acid.

6. A salt according to claim 1 wherein said amine is 6-amino-9-[2-hydroxy-3-(N-methyl-N-2-hydroxyethylamino)propyl]-purine.

7. A salt according to claim 1 wherein said amine is 6-amino-7-[2-hydroxy-3-(N-methyl-N-2-hydroxyethylamino)propyl]-purine.

8. A salt according to claim 1 wherein said acid in 3-methylpyrazole-5-carboxylic acid.

9. A pharmaceutical composition comprising a hypolipidemically effective amount of a salt according to claim 1 in combination with a pharmaceutically acceptable carrier.

10. A composition according to claim 9 in an orally administerable unit dose form, said composition containing from 0.25 to 100 mg of said salt.

11. A composition according to claim 10 containing from 0.5 to 50 mg of said salt.

12. The method of reducing hyperlipidemia in an animal which comprises administering thereto a hypolipidemically effective amount of a salt according to claim 1.

13. An amine of the formula:

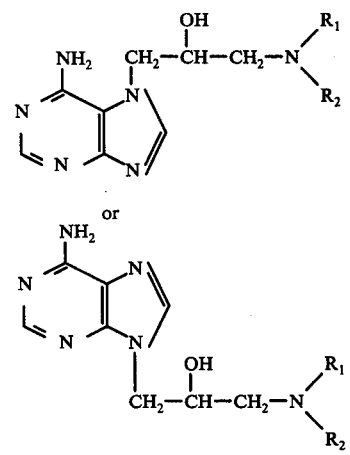

wherein
$R_1$ is alkyl of 1 to 4 carbon atoms, hydroxyalkyl of 2 to 4 carbon atoms or alkoxyalkyl of 2 to 6 carbon atoms; and
$R_2$ is hydrogen, alkyl of 1 to 4 carbon atoms; hydroxyalkyl of 2 to 4 carbon atoms or alkoxyalkyl of 2 to 6 carbon atoms.

* * * * *